Figure 1:
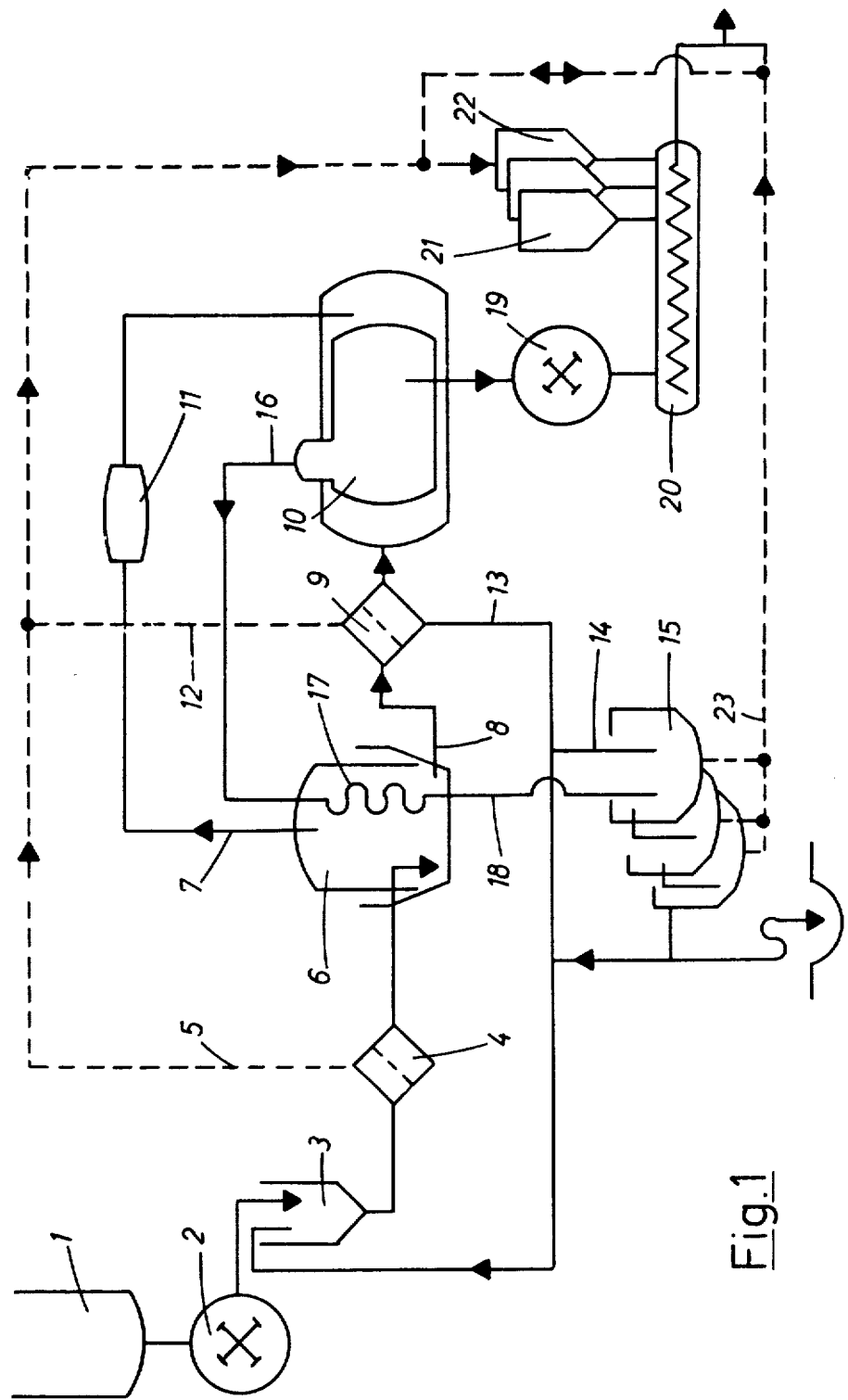

United States Patent [19]

Arsovic

[11] 4,369,194
[45] Jan. 18, 1983

[54] PROCESS FOR TREATING MANURES
[75] Inventor: Hans M. Arsovic, Baden-Baden, Fed. Rep. of Germany
[73] Assignee: Societe Agricole et Fonciere S.A.F. S.A., Switzerland
[21] Appl. No.: 201,399
[22] PCT Filed: Mar. 7, 1980
[86] PCT No.: PCT/EP80/00016
 § 371 Date: Oct. 17, 1980
 § 102(e) Date: Oct. 17, 1980
[87] PCT Pub. No.: WO80/01922
 PCT Pub. Date: Sep. 18, 1980
[30] Foreign Application Priority Data
 Mar. 14, 1979 [CH] Switzerland .................. 2405/79
[51] Int. Cl.³ .............................................. A23L 1/31
[52] U.S. Cl. ..................................... 426/59; 426/807;
 426/55; 71/10; 71/21; 48/197 A; 210/603;
 210/609; 210/630; 210/903; 435/167; 435/813;
 435/819
[58] Field of Search ................................ 71/8–10,
 71/12, 13, 21, 23; 48/197 A; 210/603, 609, 630,
 903; 426/55, 56, 807, 59; 435/167, 813, 819

[56] References Cited
U.S. PATENT DOCUMENTS 3,838,199 9/1974 Coe et al. .......................... 426/55
3,953,327 4/1976 Parker ......................... 210/630 X
4,198,211 4/1980 Shattock ....................... 210/603 X
4,252,901 2/1981 Fischer et al. ..................... 71/10 X

FOREIGN PATENT DOCUMENTS 2752271 6/1978 Fed. Rep. of Germany ......... 71/10
2827474 2/1979 Fed. Rep. of Germany ......... 71/10
1377983 12/1974 United Kingdom ................... 71/21

Primary Examiner—Ferris H. Lander
Attorney, Agent, or Firm—Robert E. Burns; Emmanuel J. Lobato; Bruce L. Adams

[57] ABSTRACT

The manure, which has been previously finely ground, is diluted (3) so as to form a liquid mixture containing not more than 4% of solid material. This mixture is fed into a bioreactor (6) of which the gas is used to feed the burner (11) of a dryer (10) in which the manure particles are dried. Before and after passage of the mixture into the bioreactor, filaments and fibres are separated (4,9). At least part of the liquid separated in the second separator (9) is recycled (13) in the initial liquid mixture. The energy of the water vapor from the drying is used to activate the bioreactor (16). The residual liquid not recycled is subjected to a nitrifying/de-nitrifying treatment (15). The residual mud may be collected (23) and mixed with the dried product, as well as the fibres and filaments eliminated. The mud, the filaments and the fibres, rich in proteins, may be used directly as foodstuff for cattle. The other residual product are appropriate for use as fertilizers.

4 Claims, 2 Drawing Figures

PROCESS FOR TREATING MANURES

The invention has for its object a method of treating manures, whatever they be, notably bovine, ovine or porcine manures, which consists in diluting the manure, introducing the resulting liquid mixture into a bioreactor in order to produce biogas, separating the solid manure particles from the liquid, and drying the recovered manure particles in a burner-type drier fed with biogas from the bioreactor, at least one fraction of the separated liquid being recycled and utilized for diluting the manure, all the process aiming at producing high-protein residues usable as cattle food and residues usable as fertilizers.

A plant of this character is disclosed in the U.S. Pat. No. 3,838,199. In this plant the liquid mixture containing at least 10% of solid matter, must be kept during 12½ days in the bioreactor and all the residual liquid is recycled. However, such a plant can only be operated with extremely clean manures, that is, free of straw or other vegetable or mineral waste, but such conditions are not found in actual practice.

On the other hand, the amount of recycled water is too high and causes the plant to be rapidly choked up due to the excess of inorganic salts. This choking effect should take place after about 15 days. Moreover, the dwelling time in the bioreactor is too long. This long dwell not only requires a very large gas-holder, but causes a floating layer of dead bacteria to develop in the bioreactor and choke the system. Finally, the important problem of ammonia treatment is not tackled.

A similar process, but without any recycling of the residual liquid, is disclosed in the U.S. Pat. No. 3,973,043. It is also contemplated therein that the liquid mixture contains at least 10% by weight of solid matter. The dwell in the bioreactor is at least 10 days. It is necessary to discharge the bioreactor periodically, and this implies closing down the plant. It is contemplated to utilize as such, as cattle food, the residue from the anaerobic fermentation, and this is attended by a risk that this residue is not sterile. It is also contemplated to utilize the waste-water such as, as a fertilizer. Now this waste water is likely to cause a nitrification of the soil. In addition, the transport of such waste-water may be prohibited for in many instances waste-water is not sterile.

A water nitrification/denitrification process has been proposed in the French Pat. No. 898,669. However, it is applicable only to drinking water having a low ammonia content. Now, in a plant such as the one constituting the subject-matter of the invention, very high ammonia concentrations are found in waste water. In the plant according to the prior art a sand-filled nitrifier is used, but this is detrimental in that it retains dead matters and must be washed periodically.

It is the object of the present invention to provide a method and a plant for carrying this method, adapted to be utilized under actual service conditions, with a high efficiency, eliminating any risk of choking or jamming by reducing the dwell in the bioreactor and producing sterile residues, notably sterile and denitrified waste-water which can be discharged directly into the town sewage system.

This object can be attained with the method according to the invention.

By combining a fine manure shredding step with the control of the mixture, limiting the concentration to a maximum value of 4% and re-heating the bioreactor by means of the condensate, it has been possible to reduce the dwell in the bioreactor to four days and even less, according to cases, and this four-days dwell gave a gas yield of 200 cu.cm./gr., a result equivalent to 24 days according to the diagrams prepared by Prof. W. Baader, Braunschweig, published by "Biogas in Theorie und Praxis", KTBL. The production of methane begins even on the first day. The thermal drying energy is utilized directly and twice by the water vapor and its condensate, firstly in the bioreactor, then in the nitrification-denitrification subplant, in which the supply of additional heat appears to be necessary.

The invention is also concerned with a plant for carrying out the method of the invention. This plant advantageously comprises oxidation tanks equipped with grids for increasing their efficient biological surface area and permitting the treatment of water having a very high ammonia content.

The product thus obtained, i.e. fine particles of dry manure, filaments and fibres, as well as sludge, can be sold separately or in admixture, as desired.

A preferred form of embodiment of the method will now be described by way of example with reference to the attached drawing.

FIG. 1 of the drawing illustrates diagrammatically the plant for carrying out the process, and the diagram of the various elements taking part in this process.

Figure 2:
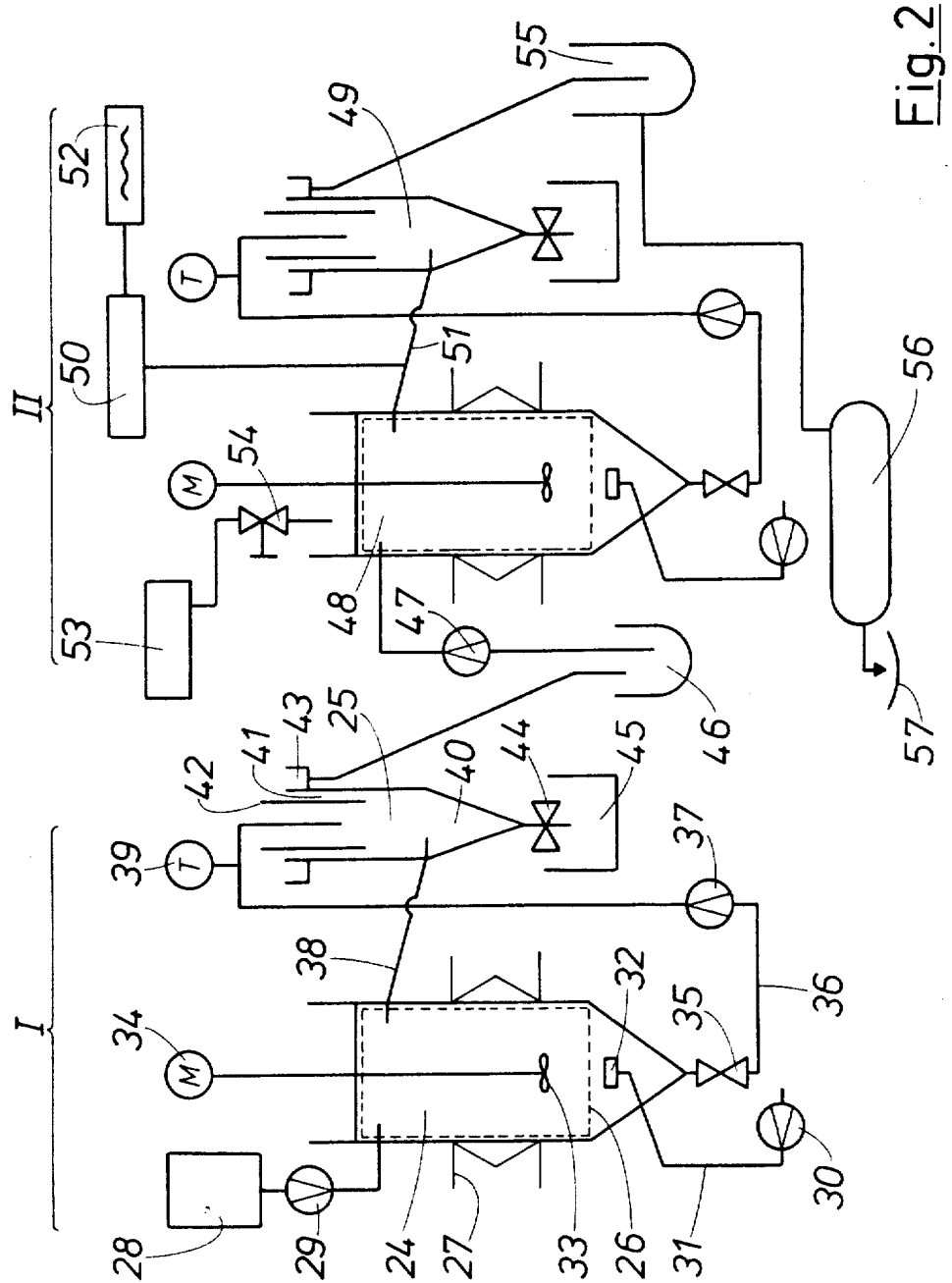

FIG. 2 illustrates diagrammatically the nitrification and denitrification subplant.

The manure supplied directly from the farming cultivation and stock-breeder is poured into a tank or hopper 1. It is then finely ground in a special grinder 2, preferably a universal Bremey 31 grinder manufactured by Meyer Mülembau AG, Solothurn (Switzerland), which is advantageous in that it does not cut but tears and shreds the material, thus increasing its surface area and ensuring an improved attack thereof by the bio-degradation organisms. The ground manure is stored in a mixing tank 3 to which liquid, such as water, is added in order to obtain a liquid mixture containing at the most 4%, and preferably 2 to 3%, of solid matter as required for producing a satisfactory bio-reaction in the bioreactor. The heavier particles, notably sand, are separated by settling during their storage in tank 1.

The liquid mixture from the mixing tank 3 contains a large amount of filaments and vegetable fibres derived from straw, as well as other light-weight solid materials other than manure. These materials are removed in a separator 4 by using a known method, such as centrifugation, mechanical settling or a flotation process. A slow-rotating Archimedean screw may also prove adequate. The solid materials thus removed at 5 contain about 20% of proteins. The filamentous materials alone contain 70% of albumin suitable for cattle consumption. The liquid still containing fine manure particles as well as filaments and other non-separated particles is fed to a bioreactor 6 known per se for producing biogas, i.e. methane at 7. In hitherto known plants a 10-day dwell is contemplated in the bioreactor for producing methane. However, due to the presence of carbon elements, it has been possible to reduce considerably this dwell time for a same gas production.

Up to now a 60% reduction of the passage time has been achieved. The liquid and the matters in suspension therein which are extracted from the bioreactor at 8 are subsequently fed to a separator 9, for example an analog separator or separator 4, in order to remove therefrom all solid substances which are dried in a drier 10, preferably a disc-type drier manufactured by Stord Bartz AS of Bergen (N), comprising a burner 11 fed with methane produced by the bioreactor 6. In the separator 9 a certain quantity of filaments 12 having a protein content of about 5% is collected. These filaments consist of undigested fibres having very small cells, which float easily. The separated liquid 13, still containing salts and undigested organic matters, is recycled in the mixing tank 3 so as to constitute the additional liquid necessary for maintaining the concentration of the liquid mixture at a value not in excess of 4%. The non-used liquid 14 is directed to a waste-water nitrification/denitrification plant 15. This plant will be described presently in detail with reference to FIG. 2.

The water vapor 16 produced by the drier 10 is condensed in a coil 17 mounted within the bioreactor 6. This water vapor will thus yield the heat necessary for bringing the reactor's content to an optimum temperature for its proper operation. The ammonia-containing condensate 18 is transfered to the nitrification/denitrification plant 15.

The dry residue from drier 10 is again finely ground in the grinder 19, identical with grinder 2, then mixed in a mixer 20, for example of the screw type together with chemical additives 21 serving the purpose of improving the quality of the manures thus obtained. One portion of the previously separated fibres and filaments may be added to the mixture at 22.

The method of neutralizing ammonia by nitrification/denitrification, applied to the non-recycled residual liquid, is applicable on the whole to all wastewaters. It is observed that ammonia concentrations in excess of 200 mg/liter inhibit the normal destruction process in waste-water treatment plants. On the other hand, in the purification technique, nitrite is considered as constituting a poison. It is therefore well to neutralize ammonia and nitrite by transformation. This operation is carried out by bacterial degradation or biosynose, i.e. by the action of bacteria. Nitrifying bacteria are autotrophic organisms utilizing only inorganic materials for their metabolism. The nitrosomone species degradate the ammonium bonds ($NH_4+$) by converting same into nitrites, while the nitrobacter species oxidizes nitrites into nitrates. These biological reactions are the optimal ones for a temperature of 30° C. and a pH=7.5.

The nitrification/denitrification plant illustrated diagrammatically in FIG. 2 comprises essentially two identical units I and II operating in the same manner. Unit I comprises an oxidation tank 24 and a settling tank 25 operating in closed-circuit conditions. The specific surface area of tank 24 is increased artificially by the addition of grids 26 creating a support on which bacteria and miscellaneous algae can develop and thus increase the biological surface area of the tanks. The tank may be heated by means of heating elements 27. The water to be treated is stored in a tank 28 from which it is pumped by means of a pump 29 into the oxidation tank 24. The oxygen necessary for the bacterial degradation in tank 24 is introduced by a pump 30, a conduit 31 and a diffuser 32. Moreover, in order to homogenize the medium a stirrer 33 driven by a motor 34 is provided. The bottom of the oxidation tank 24 is connected to the inlet of the settling tank 25 through a gate 35, a conduit 36 and a pump 37 for circulating the liquid. The return from the settling tank 25 to the oxidation tank 24 takes place via a conduit 38 according to the principle of communicating vessels. A thermostat 39 inserted in conduit 36 controls the heating elements 27 in order to maintain a temperature of the order of 27° to 30° C. in the oxidation tank 24, this temperature being the ideal one for the nitrification process.

The function of the settling tank 25 is to separate the water and sludge formed by the algae and bacteria having developed from the various polluting agents. The design of this settling tank 25 is known per se. It comprises two rest areas in which the water circulation rate as well as the movements are substantially zero, one area lying in the lower portion 40 of the tank and the other in the upper portion 41, between the outer cylindrical wall of the tank and a cylindrical dipper wall 42. Sludge settles in area 40 and it is in area 41, also called clarification area, that the water separated from sludge by overflow into an annular trough 43 is collected. The settled sludge may be collected in a receptacle 45 under control of a valve 44, and the water collected at 43 flows freely into an intermediate tank 46 from which it is sucked up by a pump 47 and fed into an oxidation tank 48 of the second unit. The oxidation tank 48 is identical with the oxidation tank 24. Similarly, the settling tank 49 is identical with the settling tank 25. The second unit II differs from the first unit I only by the presence of a pH measuring device 50 connected to the return conduit 51 and associated with a recorder 52 for continuously recording the pH value, and by a soda tank 53 associated with a valve 54 through which soda can be added to the tank 48 for regularizing the pH value.

The valve 53 may advantageously be controlled automatically from the pH measuring device 50.

The sludge deposited in the settling tank 49 is extremely light and one portion thereof tends to be carried along by flotation in the upper portion of the tank. This sludge is removed by a secondary settling receptacle 55 and the treated water is collected in a last receptacle 56 from which it is discharged into a trough 57.

The conditions of operation and exploitation of this nitrification/denitrification plant are essentially subordinate to the nature of the water to be treated, notably its organic matter content and its ammonia content.

If the organic product content is high, the first unit will be used to a large extent for the degradation of these products. It is only when the organic products have been consumed that the ammonia degradation begins. According to the ammonia contents, one shall either add a third unit identical with the first two units, or select a lower throughput.

If the organic product content is low, the ammonia degradation will occur directly in the first unit if the bacteria are adapted. Then, according to the ammonia concentration, one may either select the output through the unit or, if this concentration is very high, add a third unit identical with the first two units.

Laboratory tests have been carried out with a plant having the following characteristics:
Oxidation tank capacity: 12 liters
Settling tank capacity: 1.5 liters
Capacity of secondary settling tank: 1.5 liters
Plant throughput for an ammonia concentration of about 1 g/l: 6 to 8 liters/24 h.
Pump output of the closed circuit: 20 l/h
Oxygenation pump output: ~30 l/h This nitrification/denitrification plant differs from known plants by the very high charge with which it can operate, by the temperature range in which it operates, by the degree of elimination of the influence of carbons, and by the nitrogen transformation in the presence of such amounts of sulphur. The residual sludge consists of proteins suitable for use as cattle food.

For the complete manure treatment process, it has been possible to measure the following numerical values:

For fresh manure containing 17% of solid matter, i.e. having a 83% humidity content, 6,7% of dry substances in suspension remain in the suspension liquid delivered into the bioreactor. Theoretically, the dried substances remaining in the 7-percent solution can be converted microbiologically to the extent of 4,83%. The result of analyses show that 63% of these dried substances are converted into gas, the balance, i.e. 37% remaining in the liquid effluent 8 from the bioreactor. In this liquid one finds 0.35% of proteins corresponding to a 19.8% protein content in the dry state.

The bioreactor is capable of delivering from 80 to 120% of the energy necessary for the drying phase, respectively the evaporation, of the surplus water. Condensing the water vapor from the drier in the bioreactor and heating the biological mass in the bioreactor produces a 40% temperature rise at the drier input. Thus, the cold liquid entering the bioreactor is delivered therefrom at a temperature of about 35° C. The energy thus spared is considerable.

The balance of the energy production of the plant is approximately as follows: 1,000 kg of manure containing 17% of dry material yields 100 to 120 kg of protein-containing filaments which can be centrifuged, decanted or screened directly.

In the remaining suspensions of 70 kg/m$^3$ in a 5.3% solution, about 80 kg of material are obtained in the form of filaments, cellulose, minerals and miscellaneous residues, albumin, as well as impurities in suspension. 30% of 70 kg/m$^3$ in a 5.3% solution are converted biologically into methane, $CO_2$, acids, proteins, water and nitro compounds.

After passing through the bioreactor there remains, in addition to the residual liquid, about 150 to 180 kg of useful, i.e. commercial substance.

The increment observed between 150 kg of recovered substances per ton of manure and 150 to 180 kg per ton is subordinate to the biosynosis in the bioreactor.

The sludge recovered at 23 from the plant for the nitrification-denitrification of waste-water 15 contains up to 90% of albumin that can be digested by cattle. This sludge may be sold as food with the fibres separated at 5 and 12, or mixed with the dry product delivered by the drier in order to obtain a larger volume. According to market conditions, one may add cellulose particles or previously eliminated filaments. The dry product may be either bagged or piled up and sold.

Therefore, the method distinguish itself by a high versatility capable of eliminating market fluctuations.

I claim:

1. A method for treating manures which comprises the steps of:

finely shredding the manure, mixing the shredded manure with water in a mixer to obtain a liquid mixture containing no more than 4 percent solids, separating said liquid mixture in a first separator to remove light-weight solids from a fluid phase containing fine solids, reacting said fluid phase in a bioreactor for a period not exceeding four days and thereby generating a combustible biogas with a gas yield of about 200 cm$^3$/gm. of manure, separating fluid outflow from said bioreactor in a second separator to remove undigested solids, drying solids from said first and second separators in a drier with heat supplied at least in part by the combustion of said biogas from said bioreactor, conducting water vapor from said drier to a heat exchanger/condenser in said bioreactor to yield heat for maintaining the content of said bioreactor at an optimum temperature, conducting a first part of liquid from said second separator back to said mixer and a second part of said liquid to nitrification/denitrification means, and subjecting said liquid in said nitrification/denitrification means successively to bacterial degeneration and oxygenation and to a settling process for separating water from sludge.

2. A method according to claim 1, in which said finely shredded manure is mixed with sufficient water in said mixer to obtain a liquid mixture having a solid content of between 2% and 3%.

3. A method according to claim 1, in which said liquid in said nitrification/denitrification means is subjected to successive first and second bacterial degeneration and oxygenation steps with an intervening settling process for separating water from sludge.

4. A method according to claim 3, in which the temperature is controlled in said first bacterial degeneration and oxygenation step and the pH value is controlled in said second bacterial degeneration and oxygenation step.

* * * * *